US012797142B2

(12) United States Patent
Kaethner et al.

(10) Patent No.: US 12,797,142 B2
(45) Date of Patent: Nov. 17, 2026

(54) MICROBEAD SIZE-DRIVEN ADAPTIVE VESSEL VISUALIZATION FOR PLANNING EMBOLIZATION PROCEDURES

(71) Applicant: Varian Medical Systems, Inc., Palo Alto, CA (US)

(72) Inventors: Christian Kaethner, Freiburg (DE); Peter Fischer, Gerhardshofen (DE)

(73) Assignee: Varian Medical Systems, Inc., Palo Alto, CA (US)

( * ) Notice: Subject to any disclaimer, the term of this patent is extended or adjusted under 35 U.S.C. 154(b) by 121 days.

(21) Appl. No.: 18/617,144

(22) Filed: Mar. 26, 2024

(65) Prior Publication Data

US 2025/0302551 A1 Oct. 2, 2025

(51) Int. Cl.

| | |
|---|---|
| ***A61B 90/00*** | (2016.01) |
| ***A61B 17/12*** | (2006.01) |
| ***A61B 34/00*** | (2016.01) |
| ***A61B 34/10*** | (2016.01) |
| ***G06T 7/00*** | (2017.01) |
| ***G06T 7/10*** | (2017.01) |

(52) U.S. Cl.

CPC ........ *A61B 34/25* (2016.02); *A61B 17/12186* (2013.01); *A61B 90/37* (2016.02); *G06T 7/0012* (2013.01); *G06T 7/10* (2017.01); *A61B 2034/105* (2016.02); *A61B 2090/3764* (2016.02); *G06T 2207/30101* (2013.01)

(58) Field of Classification Search

CPC ............................................ G06T 2207/30101

See application file for complete search history.

(56) References Cited

U.S. PATENT DOCUMENTS

| | | | | |
|---|---|---|---|---|
| 7,113,623 | B2 * | 9/2006 | Chen | G06T 19/20 345/589 |
| 10,235,756 | B2 * | 3/2019 | Brauner | G06T 7/149 |
| 11,986,342 | B2 * | 5/2024 | Eimer | A61B 8/065 |
| 12,142,365 | B2 * | 11/2024 | Kaethner | G06V 10/776 |
| 2004/0066958 | A1 * | 4/2004 | Chen | A61B 6/466 382/128 |
| 2009/0012382 | A1 * | 1/2009 | Dutta | G06T 7/0012 600/407 |
| 2012/0150048 | A1 * | 6/2012 | Kang | G06T 7/149 600/481 |
| 2015/0302584 | A1 * | 10/2015 | Brauner | G06T 7/0016 382/128 |
| 2021/0174523 | A1 * | 6/2021 | Kaethner | G16H 30/40 |
| 2021/0361257 | A1 * | 11/2021 | Eimer | A61B 8/065 |

OTHER PUBLICATIONS

Lee et al. "Embolic Agents: Particles" Semin Intervent Radiol 2023;40:315-322. (Year: 2023).*

Painter, et al., "Pulsatile blood flow, shear force, energy dissipation and Murray's Law," Theoretical Biology and Medical Modelling, Feb. 2006, 3:31, 10 pages.

* cited by examiner

*Primary Examiner* — Angela M Hoffa

(74) *Attorney, Agent, or Firm* — Morgan, Lewis & Bockius LLP; Manita Rawat

(57) ABSTRACT

A method of planning an embolization procedure for a patient includes capturing a 3D digital image of a vessel at a target site after a contrast agent has been administered to the vessel; determining diameters of the vessel based on the digital image; and outputting a digital representation of the vessel where different colors indicate different diameters of the vessel.

20 Claims, 3 Drawing Sheets

MICROBEAD SIZE-DRIVEN ADAPTIVE VESSEL VISUALIZATION FOR PLANNING EMBOLIZATION PROCEDURES

TECHNICAL FIELD

This disclosure relates to embolization procedure planning. More specifically, the disclosure relates to a method used to predetermine vessels in which microbeads will flow or will not flow while planning an embolization procedure.

BACKGROUND

Many clinical situations benefit from regulation of the vascular, lymphatic or duct systems by restricting the flow of body fluid or secretions. For example, the technique of embolization involves the introduction of particles into the circulation to occlude blood vessels, for example, so as to either arrest or prevent hemorrhaging or to cut off blood flow to a structure or organ as a means to restrict necessary oxygen and nutrients to the targeted tissue. Permanent or temporary occlusion of blood vessels is desirable for managing various diseases and conditions.

Controlled, selective obliteration of the blood supply to tumors is also used in treating solid tumors such as renal carcinoma, bone tumor and liver cancer, among various others. The idea behind this treatment is that preferential blood flow toward a tumor will carry the embolization agent to the tumor thereby blocking the flow of blood which supplies nutrients to the tumor, causing it to shrink. Embolization may be conducted as an enhancement to chemotherapy or radiation therapy.

In a typical embolization procedure, local anesthesia is first given over a common artery. The artery is then percutaneously punctured and a catheter is inserted and fluoroscopically guided into the area of interest. An angiogram is then performed by injecting contrast agent through the catheter. Embolic particles are then deposited through the catheter. The embolic particles are chosen, for example, based on the size of the vessel to be occluded, the desired duration of occlusion, and/or the type of disease or condition to be treated, among others factors. A follow-up angiogram is usually performed to determine the specificity and completeness of the arterial occlusion.

For the intra-procedural planning of an embolization procedures (e.g. prostate artery embolization, trans-arterial chemoembolization, genicular artery embolization), a contrast-agent is injected into the target vasculature while acquiring a series of 2D X-ray images or a 3D volume. The contrast-enhanced vasculature can then be used for planning the access to the target location to be treated via embolization. The planning can be further supported by advanced image-processing, such as syngo Embolization Guidance, where the contrast-enhanced vasculature is segmented and visualized. Through the segmentation, it is possible to determine the diameter of the vessels in the target location. For the embolization itself, an embolic material, such as microbeads or microspheres, is injected to prevent further vascular blood supply to the target structure or to supply radiation or therapeutic agents to the target location. Even though most microbeads have a range of sizes as provided in a single vial, there are some brands, such as Varian's Embozene® Microspheres, that are tightly specified within 10 uniform size ranges (e.g. from 40 μm to 1300 μm).

Currently, there is no way to know the relationship between the size of the target vessels and the microbeads to be injected into the vessels. In some cases, a clinician can manually measure diameters of vessels, but only for some vessels and without getting a full understanding of all the target vessels. Thus, while planning the injection of microbeads with a particular size, there is no differentiation between affected and not affected vessels, i.e., vessels that have a large enough diameter for the microbeads to flow into during injection and those that have not. A differentiation and visual indication of target vasculature would support more precise planning of the injection and would allow a clinician to focus on affected vessels during embolization.

Thus, there is a need in the art for improved injectable particles as well as methods of treatment using the same to result in localized modification of the tumor microenvironment to increase the efficacy of the embolization therapy.

SUMMARY

The methods described herein are directed to embodiments to correlate the size of a patient's vessels to the size of microbeads used for embolization after vessel segmentation to differentiate between affected and not affected vessels and the respective visualization to support intra-procedural embolization planning. The methods can determine where certain microbeads can flow and where they cannot flow in the patient's vessels.

Various outputs of the disclosed methods provide input to assist a clinician in selecting microbeads for an embolization procedure to more closely match a microbead to the patient's vessel structure in the area targeted for embolization. An output can also recommend a microbead for the procedure.

To address the problems described above, in a disclosed embodiment, a method of vessel visualization includes capturing a digital image of a vessel tree of a patient that has been contrast-enhanced; and determining diameters of the vessel tree along the vessel tree based on the digital image.

In an aspect, the step of determining diameters of the vessel tree along the vessel tree is performed prior to an embolization treatment involving the vessel tree.

In an aspect, the step of determining diameters of the vessel tree along the vessel tree is performed by including a clinical model in a vessel segmentation algorithm.

In an aspect, the digital image is a 3D reconstruction of the vessel tree.

In an aspect, the digital image is captured via Cone-beam CT.

In an aspect, the digital image is captured via syngo DynaCT.

In an aspect, the diameters of the vessel tree are determined based on Murray's law.

In an aspect, the diameters of the vessel tree are determined based on a machine learning model.

In an aspect, the diameters of the vessel tree are determined from a centerline of vessels in the vessel tree.

The method can further include displaying a 3D graphical representation of the vessel tree on a monitor viewable by a clinician.

In an aspect, the 3D graphical representation of the vessel tree is color coded to indicate various diameters of vessels in the vessel tree.

In an aspect, the 3D graphical representation of the vessel tree is overlaid an image of an embolization target site.

The method can further include determining a diameter of microbeads to use for an embolization procedure in the patient.

In another embodiment of the present disclosure, a method of planning an embolization procedure for a patient includes capturing a 3D digital image of a vessel at a target site after a contrast agent has been administered to the vessel; determining diameters of the vessel based on the digital image; and outputting a digital representation of the vessel where different colors in the representation indicate different diameters of the vessel.

The method can further include selecting microbeads for the embolization procedure based on the diameters of the vessel.

In an aspect, color coding indicates where microbeads of a certain diameter can flow within the vessel and where the microbeads cannot flow.

The method can further include overlaying the digital representation of the vessel on a digital representation of the target site.

In another embodiment of the present disclosure, a non-transitory computer-readable medium including executable instructions that when executed by a processor cause the processor to perform: determining diameters of a vessel of a patient based on a 3D digital image of the vessel after the vessel was contrast enhanced.

In an aspect, the determining the diameters of the vessel is performed by a machine learning model.

BRIEF DESCRIPTION OF THE DRAWINGS

The features and advantages of the present disclosures will be more fully disclosed in, or rendered apparent by the following detailed descriptions of example embodiments. The detailed descriptions of the example embodiments are to be considered together with the accompanying drawings wherein like numbers refer to like parts and further wherein.

DETAILED DESCRIPTION

Figure 1:
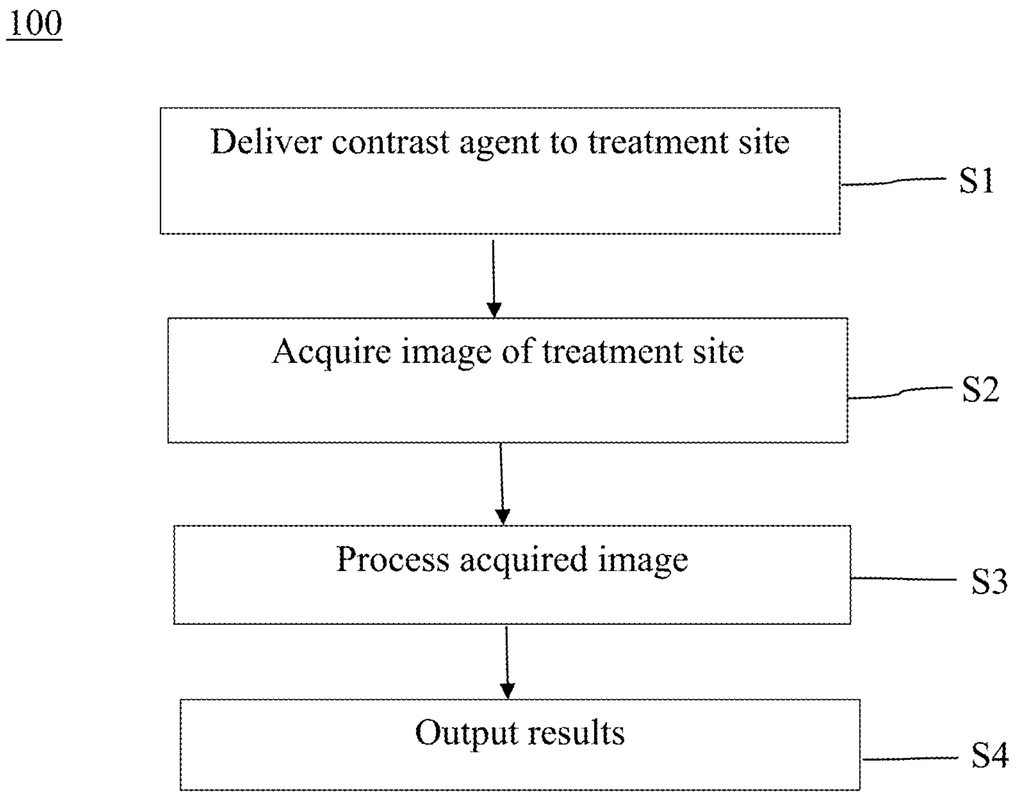
FIG. 1 is a flowchart including steps of a mapping method of imaging microbeads and determining a shunt fraction according to an embodiment of the present disclosure.

The description of the preferred embodiments is intended to be read in connection with the accompanying drawings, which are to be considered part of the entire written description of these disclosures. While the present disclosure is susceptible to various modifications and alternative forms, specific embodiments are shown by way of example in the drawings and will be described in detail herein. The objectives and advantages of the claimed subject matter will become more apparent from the following detailed description of these exemplary embodiments in connection with the accompanying drawings.

It should be understood, however, that the present disclosure is not intended to be limited to the particular forms disclosed. Rather, the present disclosure covers all modifications, equivalents, and alternatives that fall within the spirit and scope of these exemplary embodiments.

During an embolization treatment, hydrogel, tiny glass or resin microbeads including, for example, a radioactive isotope yttrium Y-90 or therapeutic agent are administered inside the blood vessels that feed a tumor or a target tissue site. At least some of the injected microbeads, via the inclusion of highly X-ray visible materials in the microbeads, are directly visible in a 3D X-ray image. To maximize the results of the procedure, it is desirable to understand how the microbeads will flow with respect to the target tissue site.

FIG. 1 is a flowchart of a method 100 of visualizing vessels at a treatment site prior to performing an embolization procedure. In step S1, a contrast agent is delivered to the treatment site. The contrast agent should be delivered upstream of the treatment site and can be provided via catheterization, injection, or by any other suitable mechanism. It is expected that the contrast agent will flow through rather quickly through tissue at the treatment site so, in step S2, an image is captured of the treatment site very shortly after the contrast agent has been administered.

Figure 2:
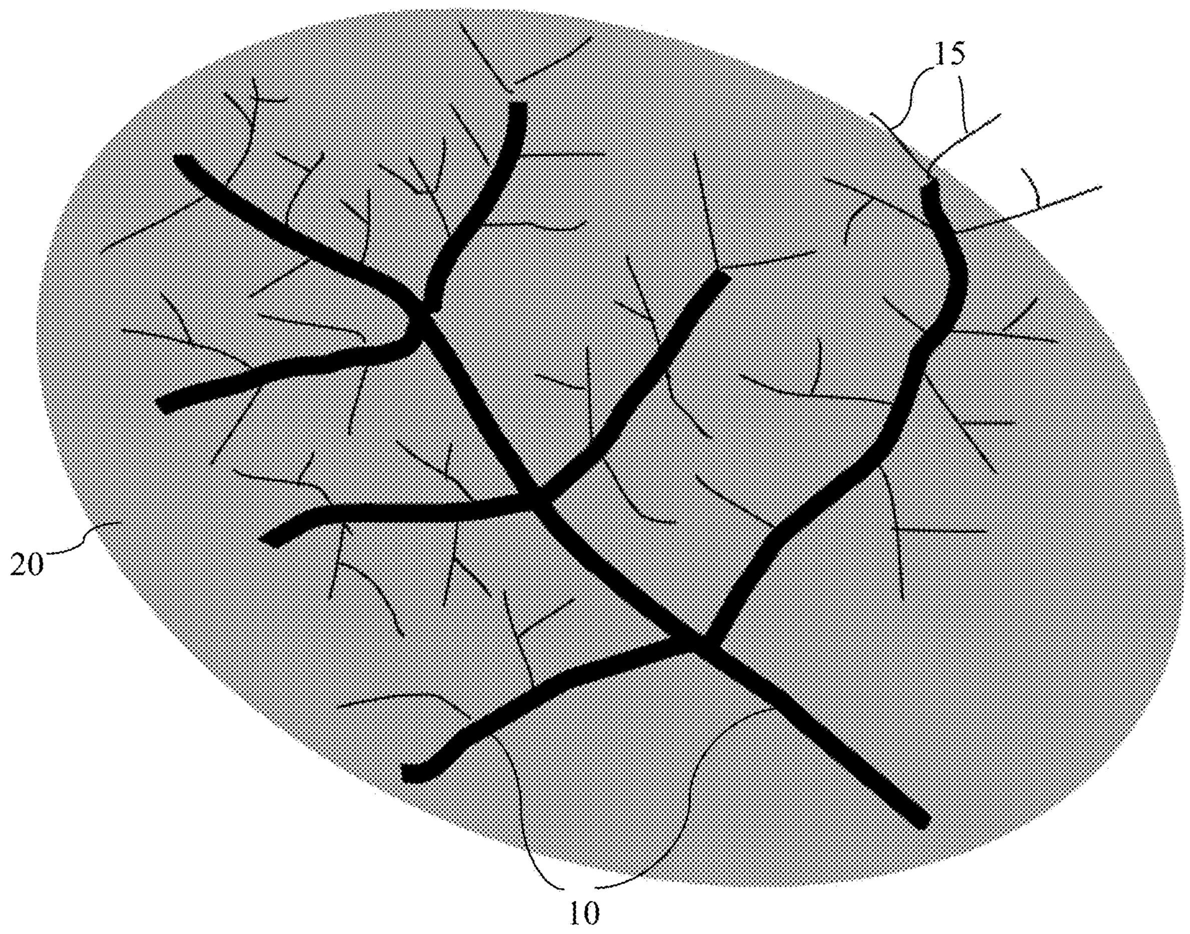
FIG. 2 represents blood vessels of an organ.

The dark lines in FIG. 2 represent blood vessels of an organ surrounded by parenchyma or tumor tissue 20, represented as a gray oval. In this example, the medium to large blood vessels 10 and the microvasculature 15 are filled with a liquid contrast agent such as an iodine solution that has been injected upstream from the tissues. It is possible to image smaller blood vessels and tissue uptake of the liquid contrast agent. This is done by either directly resolving smaller individual blood vessels and/or by calculating a bulk/spatially averaged uptake of contrast agent in tissue and smaller blood vessels.

To allow for the respective level of detail in 3D imaging with respect to the contrast-enhanced vasculature, the imaging system used to capture the image needs to provide sub-millimeter resolution. To achieve this, a high-resolution detector can be used, and no binning applied. Furthermore, super-resolution techniques, high-resolution 3D reconstruction (e.g. cone-beam computed tomography (CBCT)) with 140 μm resolution), and further image processing can be used on the acquired images. CBCT is a technology that uses a C-arm mounted flat-panel detector to produce cone-beam volume CT images in the angiography suite. The CBCT system includes a control and processing system that can be a single computer or network of computers used to control the CT system and interact with a clinician to perform image capture, image processing, data manipulation, calculations, and map generation in steps of the method 100.

Typical embolization microbead sizes range from 40 μm to 1300 μm. To provide "microbead size-driven visualization", the resolution of the imaging modality from which the vessels are derived has to be higher or in a similar range. Typical full field of view CBCT images have a resolution of 500 μm, which would be suitable for the larger microbead sizes. To cover smaller microbeads as well, special reconstruction techniques are required. An example is syngo DynaCT that achieves a resolution of 140 μm with the tradeoff of a smaller field of view. syngo DynaCT provides CT-like cross-sectional imaging by creating 3D soft tissue data sets. Where in the past it would have been necessary to transfer the patient into the CT unit, syngo DynaCT can be performed instead, directly in the angiography suite without loss of time and with no additional risk to the patient.

For these high-resolution reconstructions, there is also no binning of pixels on the X-ray detector, i.e., the full resolution of the detector is used. Usually, this is not the case in CBCT reconstruction, where it is more important to have low noise and neighboring pixels are averaged. Furthermore, there are image processing algorithms that can be run on the control and processing system to enhance the resolution of an image, which can be helpful to produce suitable high-resolution reconstructions, for example, in step S3, in which the captured image is processed.

In step S3, the captured image can be processed. Image processing can include several actions. For example, initially the captured image can be enhanced to reduce noise or improve contrast. Also, the captured image can be processed to extract information on the vessels in the target site.

An explicit vessel segmentation that contains vessel diameter information along the vessel tree is helpful to realize the adaptive visualization of the vessel structure. It is important to determine accurate vessel diameters for complete visualization. There are clinical models such as Murray's law on how diameters evolve along the vessel tree, which can be used, for example, in silico simulation of hepatic arteries. "Murray's Law states that, when a parent blood vessel branches into daughter vessels, the cube of the radius of the parent vessel is equal to the sum of the cubes of the radii of daughter blood vessels." Page R. Painter, et al., *Pulsatile bloodflow, shearforce, energy dissipation and Murray's Law,* 3 Theoretical Biology and Med. Modelling, 31, (2006). Such a model can be included in a vessel segmentation algorithm as prior knowledge to feed into another algorithm or to as a cross-check when segmentations are calculated to make sure they do not violate Murray's law.

In addition to high resolution imaging, a clinical vascular machine learning (ML) model can be included in the control and processing system and used to train an algorithm that understands the "structure" of a vessel tree and that allows for estimating the respective diameter changes in the vessel tree from proximal to distal vessel branches. In an image of the target site, vessels containing contrast agent can be in close proximity with other "bright" features in the image. Such a ML model can be trained to distinguish what in the digital image is a vessel and what is not a vessel. For example, an ML model can be trained to learn that a vessel is tubular with a changing diameter by indicating a centerline of vessels in an image. Training can include providing the ML model with multiple examples of datasets with annotated centerlines. The ML model can calculate a diameter of a vessel as being perpendicular to the centerline along the centerline and indicate that blood flow is in a direction in which the diameter of the vessel is decreasing.

Vessel visualization can take into account an estimation of the behavior of the microbeads after administration. Based on biochemical models and respective simulations, it can be predicted if and how the microbeads change their size after injection. Microbeads can be elastic and compressible. This property might permit the microbeads to flow further than would be expected given only their specified diameter values. Similarly, vessels are not rigid but can change shape and expand, e.g. due to changes in blood pressure.

Note that the diameter of some batches of microbeads can be tightly calibrated while the diameter of other batches is not. If there is a large variability in diameters of microbeads in a batch, there is more randomness how far the microbeads can travel within vessels.

The information about the vessel tree and the microbeads gathered from the contrast agent administration can then be paired to provide an output for a clinician. In step S4, the output can be provided to the clinician performing the embolization. One output can be microbead-size driven adaptive vessel visualization. For example, a vessel tree with associated diameter information can be derived from the processing in step S3. With this information, the clinician can select a microbead with known diameter and compressibility parameters for administration to the target site.

In some embodiments, the control and processing system can display a 3D graphical representation of the vessel tree on a monitor viewable by the clinician that can be color coded to indicate various diameters of vessels in the vessel tree.

Figure 3:
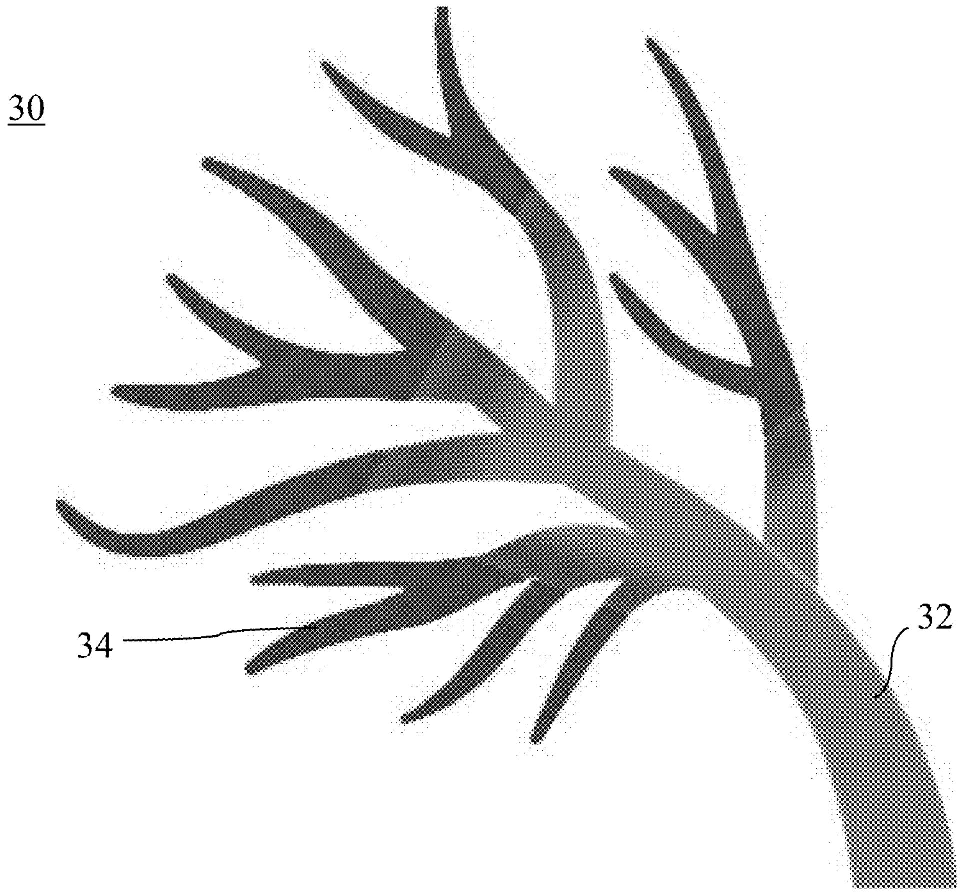
FIG. 3 is a graphical representation of a vessel tree, according to an embodiment of the present disclosure.

In some embodiments, a graphical representation of the vessel tree can be provided to indicate how far selected microbeads could reach in different vessel branches. Although not in color, FIG. 3 shows in grayscale how this information can be presented in a graphic of a vessel tree 30. For example, for a selected microbead with a given diameter, vessels where the microbeads can easily flow 32 can be shown at one gray level or color and vessels with diameters that that are too small for the for the size of the microbeads 34 can be shown at a different gray level or color. In some embodiments, the colors can indicate where microbeads of a diameter can flow and where they cannot flow, in a go/no-go fashion.

In some embodiments, on a monitor, a digital representation of the vessel tree can overlay a digital image of the target site. For example, the digital representation of the vessel tree can include different colors representing the different vessel diameters. In some embodiments, a digital representation can include only vessels that have a diameter compatible with a certain bead size. In some embodiments, a determination and recommendation can be made for what diameter microbeads to use for the patient and procedure.

The foregoing is provided for purposes of illustrating, explaining, and describing embodiments of these disclosures. Modifications and adaptations to these embodiments will be apparent to those skilled in the art and may be made without departing from the scope or spirit of these disclosures.

Additionally, or alternatively, a portion of the above-described method can be implemented as a non-transitory computer-readable storage medium embodied thereon a program executable by a processor for performing steps or a method of various embodiments.

Also, the various methods or processes outlined herein can be coded as software that is executable on one or more processors that employ any one of a variety of operating systems or platforms. Additionally, such software can be written using any of a number of suitable programming languages and/or programming or scripting tools, and also can be compiled as executable machine language code or intermediate code that is executed on a framework or virtual machine. Typically, the functionality of the program modules can be combined or distributed as desired in various embodiments.

Also, the embodiments of the disclosure can be embodied as a method, of which an example has been provided. The steps or acts performed as part of the method can be ordered in any suitable way. Accordingly, embodiments can be constructed in which steps are performed in an order different than illustrated, which can include performing some steps concurrently, even though shown as sequential steps in illustrative embodiments.

What is claimed is:

1. A method of vessel visualization for an embolization procedure, the method comprising:

capturing a digital image of a vessel tree of a patient that has been contrast-enhanced;

determining a respective plurality of diameters of a plurality of vessel segments of the vessel tree based on the digital image;

comparing the respective plurality of diameters of the plurality of vessel segments to a diameter of a selected microbead type to use for an embolization procedure, in view of a compressibility parameter of the selected microbead type or an expansion parameter of each of the plurality of vessel segments; and presenting a visualization of the plurality of vessel segments based on the comparison of the respective plurality of diameters of the plurality of vessel segments to the diameter of the selected microbead type, in view of the compressibility parameter of the selected microbead type or the expansion parameter of each of the plurality of vessel segments, wherein the visualization indicates where the selected microbead type can flow within the plurality of vessel segments and where the selected microbead type cannot flow within the plurality of vessel segments.

2. The method of claim 1, wherein the digital image is a 3D reconstruction of the vessel tree.

3. The method of claim 1, wherein the respective plurality of diameters of the plurality of vessel segments of the vessel tree are determined based on a machine learning model.

4. The method of claim 1, further comprising displaying a 3D graphical representation of the vessel tree on a monitor viewable by a clinician.

5. The method of claim 4, wherein the 3D graphical representation of the vessel tree is overlaid on an image of an embolization target site.

6. The method of claim 1, wherein presenting the visualization of the plurality of vessel segments comprises presenting a plurality of colors corresponding to the comparison of the respective plurality of diameters of the plurality of vessel segments to the diameter of the selected microbead type, wherein a color coding indicates where the selected microbead type can flow within one or more of the plurality of vessel segments and where the selected microbead type cannot flow within one or more of the plurality of vessel segments.

7. The method of claim 1, further comprising determining the diameter of the selected microbead type to use for the embolization procedure in the patient.

8. The method of claim 1, wherein the visualization of the plurality of vessel segments includes a first visualization of a first portion of the plurality of vessel segments capable of receiving the selected microbead type based on the comparison of the respective plurality of diameters of the plurality of vessel segments to the diameter of a selected microbead type.

9. The method of claim 8, wherein the first visualization of the first portion of the plurality of vessel segments presenting a first color corresponding to the first portion of the plurality of vessel segments capable of receiving the selected microbead type.

10. The method of claim 8, wherein the visualization of the plurality of vessel segments includes a second visualization of a second portion of the plurality of vessel segments capable of preventing flow of the selected microbead type based on the comparison of the respective plurality of diameters of the plurality of vessel segments to the diameter of a selected microbead type.

11. The method of claim 10, wherein the second visualization of the second portion of the plurality of vessel segments presenting a second color corresponding to the second portion of the plurality of vessel segments capable of preventing flow of the selected microbead type.

12. The method of claim 1, wherein determining the respective plurality of diameters of the plurality of vessel segments is based on a clinical model in a vessel segmentation algorithm.

13. The method of claim 1, wherein determining the respective plurality of diameters of the plurality of vessel segments is based on Murray's law.

14. A method of planning an embolization procedure for a patient, comprising:

capturing a 3D digital image of a vessel at a target site after a contrast agent has been administered to the vessel;

determining a plurality of diameters of the vessel based on the digital image;

comparing the plurality of diameters of the vessel to a diameter of a selected microbead type to use for the embolization procedure, in view of a compressibility parameter of the selected microbead type or an expansion parameter of each of the plurality of vessel segments; and outputting a digital representation of the vessel based on the comparison of the plurality of diameters of the vessel to the diameter of the selected microbead type, in view of the compressibility parameter of the selected microbead type or the expansion parameter of each of the plurality of vessel segments, wherein the visualization indicates where the selected microbead type can flow within the plurality of vessel segments and where the selected microbead type cannot flow within the plurality of vessel segments.

15. The method of claim 14, further comprising selecting the microbead type for the embolization procedure based on the plurality of diameters of the vessel.

16. The method of claim 14, wherein outputting the digital representation of the vessel comprises presenting a plurality of colors corresponding to the comparison of the plurality of diameters of the vessel to the diameter of the selected microbead type.

17. The method of claim 14, further comprising overlaying the digital representation of the vessel on a digital representation of the target site.

18. A non-transitory computer-readable medium including executable instructions that when executed by a processor cause the processor to perform:

determining a plurality of diameters of a vessel of a patient based on a 3D digital image of the vessel after the vessel was contrast enhanced;

comparing the plurality of diameters of the vessel to a diameter of a selected microbead type to use for an embolization procedure, in view of a compressibility parameter of the selected microbead type or an expansion parameter of each of the plurality of vessel segments; and causing presentation of a digital representation of the vessel for an embolization procedure based on the comparison of the plurality of diameters of the vessel to the diameter of a selected microbead type, in view of the compressibility parameter of the selected microbead type or the expansion parameter of each of the plurality of vessel segments, wherein the visualization indicates where the selected microbead type can flow within the plurality of vessel segments and where the selected microbead type cannot flow within the plurality of vessel segments.

19. The non-transitory computer-readable medium of claim 18, wherein the determining the plurality of diameters of the vessel is performed by a machine learning model.

20. The non-transitory computer-readable medium of claim 18, wherein causing presentation of the digital representation of the vessel comprises causing presentation of a plurality of colors corresponding to the comparison of the plurality of diameters of the vessel to the diameter of the selected microbead.

* * * * *